(12) United States Patent
Korkala et al.

(10) Patent No.: US 10,314,506 B2
(45) Date of Patent: Jun. 11, 2019

(54) HEART ACTIVITY SENSOR STRUCTURE

(71) Applicant: Polar Electro Oy, Kempele (FI)

(72) Inventors: Seppo Korkala, Kempele (FI); Elias Pekonen, Oulu (FI); Juhani Kemppainen, Oulu (FI); Pekka Rytky, Oulu (FI); Jarmo Saaski, Kempele (FI)

(73) Assignee: POLAR ELECTRO OY, Kempele (FI)

( * ) Notice: Subject to any disclaimer, the term of this patent is extended or adjusted under 35 U.S.C. 154(b) by 457 days.

(21) Appl. No.: 14/643,759

(22) Filed: Mar. 10, 2015

(65) Prior Publication Data
US 2015/0223716 A1 Aug. 13, 2015

Related U.S. Application Data

(63) Continuation-in-part of application No. 14/274,137, filed on May 9, 2014.

(30) Foreign Application Priority Data

May 15, 2013 (EP) .................................... 13167788

(51) Int. Cl.
| | |
|---|---|
| *A61B 5/0402* | (2006.01) |
| *A61B 5/0424* | (2006.01) |
| *A61B 5/0408* | (2006.01) |
| *H05K 9/00* | (2006.01) |
| *H05K 3/00* | (2006.01) |
| *H05K 3/10* | (2006.01) |
| *A61B 5/0245* | (2006.01) |
| *A61B 5/00* | (2006.01) |

(52) U.S. Cl.
CPC .......... *A61B 5/0424* (2013.01); *A61B 5/0245* (2013.01); *A61B 5/04085* (2013.01); *H05K 3/005* (2013.01); *H05K 3/10* (2013.01); *H05K 9/0079* (2013.01); *A61B 5/6831* (2013.01); *A61B 2562/164* (2013.01);
(Continued)

(58) Field of Classification Search
CPC ... A61B 5/0006; A61B 5/6831; A61B 5/0402; A61B 5/0478; A61B 5/0245; A61B 5/7203; A61B 2562/182; A61N 1/0492; A61N 1/0484
USPC ................ 600/372, 382, 374, 386, 388–393, 600/508–509
See application file for complete search history.

(56) References Cited

U.S. PATENT DOCUMENTS

| | | | |
|---|---|---|---|
| 3,534,727 A | 10/1970 | Roman | |
| 4,122,843 A | 10/1978 | Zdrojkowski | |

(Continued)

FOREIGN PATENT DOCUMENTS

| | | |
|---|---|---|
| EP | 2057943 A1 | 5/2009 |
| GB | 2438953 A | 12/2007 |
| WO | 2012/104484 A1 | 8/2012 |

OTHER PUBLICATIONS

European Search Report, Application No. EP 13 16 7788, dated Nov. 21, 2013, 2 pages.

*Primary Examiner* — Joseph A Stoklosa
*Assistant Examiner* — Brian M Antiskay
(74) *Attorney, Agent, or Firm* — FisherBroyles, LLP (57) ABSTRACT

A heart activity sensor structure includes a flexible substrate being substantially non-conductive, at least two electrodes printed on one side of the flexible substrate and configured to be placed against a skin of a user in order to measure biometric signals related to heart activity, and an electrostatic discharge shield printed on opposite side the flexible textile substrate, compared to the printing of the at least two electrodes, for protecting the at least two electrodes from static electricity.

20 Claims, 6 Drawing Sheets

(52) U.S. Cl.
CPC ..... *A61B 2562/182* (2013.01); *Y10T 29/4913* (2015.01); *Y10T 29/49155* (2015.01)

(56) References Cited

U.S. PATENT DOCUMENTS

| | | | |
|---|---|---|---|
| 4,763,660 | A | 8/1988 | Kroll et al. |
| 5,483,967 | A | 1/1996 | Ohtake |
| 5,491,474 | A | 2/1996 | Suni et al. |
| 5,782,241 | A | 7/1998 | Felblinger et al. |
| 6,327,486 | B1 | 12/2001 | Nissila et al. |
| 6,453,186 | B1 | 9/2002 | Lovejoy et al. |
| 7,146,228 | B2 * | 12/2006 | Nielsen ............... A61B 5/0408 607/142 |
| 7,680,523 | B2 | 3/2010 | Rytky |
| 7,966,052 | B2 * | 6/2011 | DeFusco .............. A61B 5/0245 600/386 |
| 8,116,841 | B2 * | 2/2012 | Bly ..................... A61B 5/0205 600/391 |
| 8,190,230 | B2 | 5/2012 | Rytky |
| 2004/0073104 | A1 * | 4/2004 | Brun del Re ........ A61B 5/0408 600/372 |
| 2006/0030767 | A1 * | 2/2006 | Lang ................... A61B 5/04087 600/372 |
| 2007/0285868 | A1 * | 12/2007 | Lindberg ............. A61B 5/0245 600/382 |
| 2008/0287767 | A1 * | 11/2008 | Pasveer ............... A61B 5/0408 600/372 |
| 2010/0160763 | A1 | 6/2010 | Tsai et al. |
| 2013/0178728 | A1 | 7/2013 | Vandermeiden et al. |
| 2013/0345539 | A1 * | 12/2013 | Quintanar .......... A61B 5/04085 600/385 |
| 2014/0100432 | A1 * | 4/2014 | Golda ................ A61B 5/04325 600/301 |
| 2015/0173639 | A1 * | 6/2015 | Ichida ................. A61B 5/0408 600/397 |

\* cited by examiner

HEART ACTIVITY SENSOR STRUCTURE

CROSS-REFERENCE TO RELATED APPLICATIONS

This application is a continuation-in-part of pending U.S. patent application Ser. No. 14/274,137 filed on May 9, 2014, which is incorporated herein by reference. This application claims priority to European Patent Application No. EP13167788.2 filed on May 15, 2013, which is incorporated herein by reference.

BACKGROUND

Field

The invention relates generally to heart activity sensors. More particularly, the invention relates to a structure of the heart activity sensor used while exercising.

Description of the Related Art

It is common to measure heart activity while exercising in order to better monitor the effect of the exercise by the exerciser. The measuring may comprise, for example, determining the heart rate or the heart rate variation of the exerciser. Typically this is done by wearing a heart rate activity sensor having electrodes against the skin of the exerciser. However, the conditions for measuring the heart activity while exercising are harsh.

SUMMARY

According to an aspect of the invention, there is provided a heart activity sensor structure as specified in claim 1.

According to an aspect of the invention, there is provided a method as specified in claim 17.

Some embodiments are defined in the dependent claims.

BRIEF DESCRIPTION OF THE DRAWINGS

In the following, the invention will be described in greater detail with reference to the embodiments and the accompanying drawings, in which FIGS. 1A, 1B, 2, and 3 present a heart rate sensor structure to which the embodiments are applicable to;

FIGS. 10A, 10B, and 100 illustrate some embodiments of the invention.

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

As said, it is common to measure heart activity while exercising in order to better monitor the effect of the exercise by the exerciser. Typically the measuring takes place with a heart rate activity sensor having electrodes against the skin of the exerciser. The location of the skin may be, e.g. the chest of the exerciser. The electrodes may measure voltage variations on the skin wherein the variations are due to the activity of the heart muscle. As a result, an electrocardiogram (ECG) signal may be generated. From the ECG signal, a variety of information may be derived. These include heart rate or heart rate variation, for example.

The voltage changes may be in the range of millivolts, thus making the detection of the changes relatively difficult. Further, the conditions for measuring the heart activity while exercising are harsh due to, e.g., movement of the exerciser. At least partly for this reason, it is known to use a flexible textile as a substrate for mounting the electrodes which are placed against the chest of the exerciser. This is because the flexible textile is comfortable to the user compared to an integrated heart activity sensor structure. Furthermore, a flexible textile adapts better to the body shape of the exerciser and thereby ensures a better electrode contact to skin of the exerciser. An integrated heart activity sensor structure is disclosed in U.S. Pat. Nos. 5,491,474 and 6,327,486 which are hereby incorporated by reference.

The integrated heart activity sensor structure is significantly different than a sensor structure applying the flexible textile in the point of view of the functionality and from the point of view of the implementation and assembly. For example, in the integrated heart activity sensor, electrodes and transmitter electronics are both functional entities molded into a single plastic casing. The plastic casing structure is simple, durable and relatively easy to manufacture. However, the structure is relatively rigid, thus having a negative impact on the user experience. On the contrary, in the sensor structure applying the flexible textile substrate, the electrode structure is typically implemented with conductive plastic or textile applied on an elastic strap.

Figures 1A, 1B:
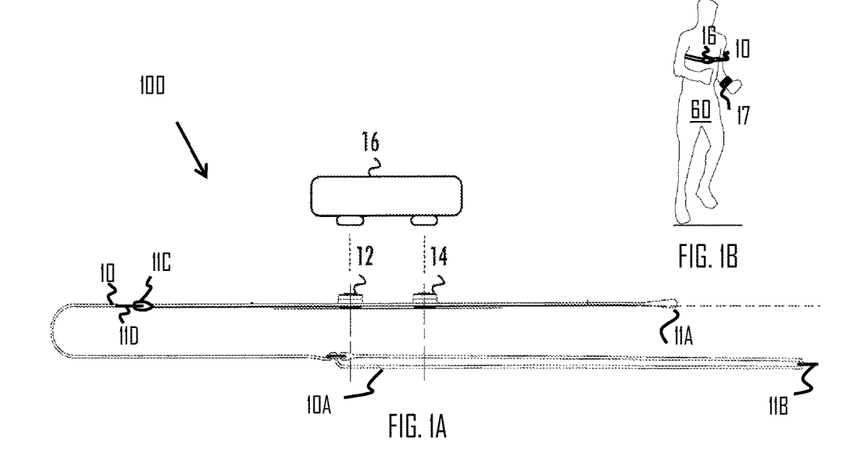

With reference to an embodiment shown in FIGS. 1A and 1B, let us consider an embodiment of a heart activity sensor structure 100 to which embodiments of the invention may be applied. The heart activity sensor structure 100 may be attached to, e.g., a strap 10, which the exerciser 60 may wear around his/her body, such as chest, in order to hold electrodes, which are comprised in the heart activity sensor structure 100, firmly against the skin 32 during the exercise. The exerciser 60 is the user of the heart activity sensor structure 100. The heart activity sensor structure 100 may comprise fastening elements 11A and 110 for detachably fastening/connecting the heart activity sensor structure 100 to fastening elements 11B and 11D of the strap 10, respectively. The strap 10 may comprise a length adjustment portion 10A adjusting the length of the strap by the exerciser 60. In an embodiment, the heart activity sensor structure 100 comprises the strap 10. It should be noted that the heart activity sensor structure 100 may alternatively be attached to a garment, such as a shirt, a top, a bra, a wristband or trousers, instead of the strap 10. In an embodiment, the garment is a glove, sock, a shirt arm, or a trouser leg.

The heart activity sensor structure 100 may comprise one or more skin electrodes used to receive a physiological signal from the skin of the user 60, and an electronic circuit may be used to process and measure the physiological signal. The electronic circuit may be installed to an electronics module 16 which may be fixed or detachably attached to the strap 10 through instant connectors 12, 14, such as press stud connectors. The electronics module 16 may further comprise a battery for powering the heart activity sensor structure 100, wherein the battery may be rechargeable or disposable.

The electronics module 16 may also comprise a wireless transmitter circuitry. Then, the measuring device may realize exercise data transmission to a training computer 17, such as to a wrist watch or to a portable receiver, e.g. a mobile phone. In an embodiment, the data transmission carries exercise data to the training computer 17. In an embodiment, the transmitted signal may carry, for instance, ECG information. In an embodiment, the electronics module 16 may be configured to measure, for instance, a physiological signal such as an electromyogram (EMG) from the skin of the user 60. In an embodiment, the heart activity sensor structure 100 may also comprise a receiver for reception of data wirelessly from another device, such as from the training computer 17. In an embodiment, the received data may comprise information needed for upholding the communication connection and/or information needed for reconfiguring the electronics module 16. Thus, the communication link to/from the electronic module 16 may, in an embodiment, be bi-directional.

Figure 2:
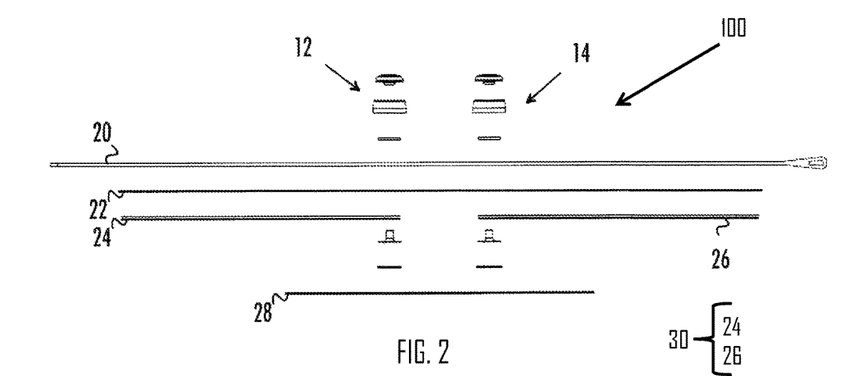
Figure 3:
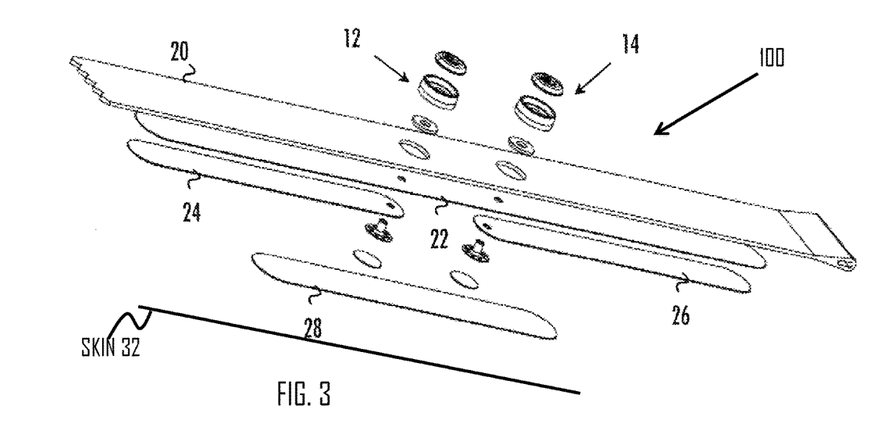

Let us now consider the structure of the heart activity sensor structure 100 in greater detail with reference to an embodiment illustrated in FIGS. 2 and 3. FIGS. 2 and 3 illustrate different explosion views of the components of the heart activity sensor structure 100, wherein FIG. 2 is a side view, and FIG. 3 is a perspective view. Referring to FIGS. 2 and 3, the heart activity sensor structure 100 comprises the flexible textile substrate 20, also known as a base layer or a supporting layer. The flexible textile substrate 20 may form the base of the heart activity sensor structure 100, and the flexible textile substrate 20 may comprise textile that supports the heart activity sensor structure 100. The flexible textile substrate 20 may comprise woven or knitted textile with elastic components, such as rubber and/or thermoplastic. The flexible textile substrate 20 may form a substrate for mounting at least the electrodes 24, 26. The physical dimensions of the flexible textile substrate 20 may be in the order of 15 cm times 2 cm (length×width).

In an embodiment, the flexible textile substrate 20 is bendably flexible (e.g. flexible so that the textile substrate 20 may be bent, flexed or twisted without breaking). In an embodiment, the flexible textile substrate 20 is stretchably flexible (e.g. flexible so that it may be stretched in longitudinal and/or transversal direction).

The heart activity sensor structure may further comprise an electrode layer 30 comprising one or more electrodes 24, 26. The at least two electrodes 24, 26 may be applied on one side of the flexible textile substrate 20 and configured to be placed against (contact) the skin 32 of the exerciser 60 either directly or indirectly. The electrodes 24, 26 may measure biosignals related to heart activity, such as ECG signals, from the skin 32 of the exerciser 60 and convey the detected electric signals to the electronics module 16 connected to the connectors 12, 14. The electrodes 24, 26 may be made at least partially of a conductive material, e.g. conductive silicon, conductive thermoplastic and/or conductive yarn. The connectors 12, 14 may be disposed to penetrate the flexible textile substrate 20 and any layer between the flexible textile substrate 20 and the electrode layer 30 to provide a galvanic connection between the electrodes 24, 26 and the electronics module 16 disposed on opposite sides of the flexible textile substrate 20. In the embodiment shown in FIGS. 2 and 3, the connectors 12, 14 penetrate also the electrode layer 30, e.g. each electrode 24, 26.

An intermediate insulation layer 22 may be provided as an intermediate layer between the flexible textile substrate 20 and the electrode layer 30. The intermediate insulation layer 22 functions as an electric insulation layer insulating the electrode layer 30 from the flexible textile substrate 20. However in an embodiment, there is no need for the intermediate insulation layer 22 in case the flexible textile substrate 20 is not electrically conductive or is not directly contacting the electrodes. It should be noted though that the flexible textile substrate 20 may become electrically conducting after absorbing moisture during the exercise.

The definition of the electrode layer 30 should be interpreted broadly to cover an electrode layer comprising at least two skin electrodes 24, 26 which may be electrically isolated from each other. In an embodiment, one of the at least two skin electrodes 24, 26 may be coupled to a ground, and a physiological signal delivered by at least one other skin electrode may be amplified and measured with respect to the ground. Alternatively, a difference signal detected between the skin electrodes 24, 26 may be amplified and measured with respect to the ground. The ground level may be defined by a skin 32 or a user's body part, such as chest or arm. The electrodes module 16 may comprise a differential amplifier to perform the amplifying of the difference signal.

When the number of electrodes 24, 26 is higher than one, the electrodes 24, 26 may be electrically isolated/insulated from each other. The electrical isolation from a surface contacting the skin 32 of the exerciser 60 may be achieved by providing a skin insulation layer 28 such that the electrodes 24, 26 are at least partially disposed between the skin isolation layer 28 and the flexible textile substrate 20. The skin isolation layer 28 reduces a short circuit between the electrodes 24, 26 through the skin 32 of the exerciser 60. The skin insulation layer 28 comprises insulating material, such as thermoplastic material, to carry out the isolation. In the case the number of electrodes 24, 26 is higher than two, the skin insulation layer 28 may in some embodiments comprise a plurality of separate insulating portions to insulate the different electrodes 24, 26 from each other.

Figure 4A:
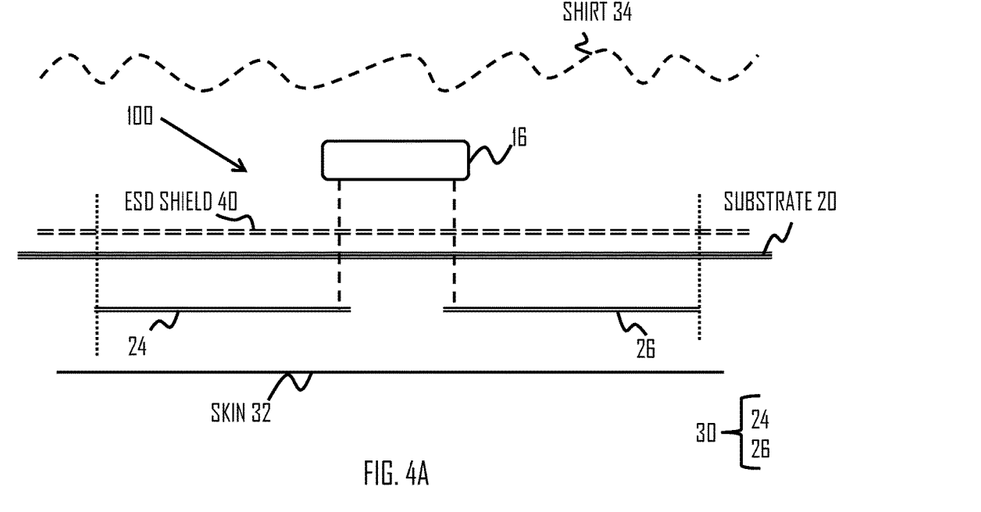
FIGS. 4A and 4B represent an electrostatic discharge (ESD) shield applied to the heart rate sensor structure according to some embodiments.
Figure 4B:
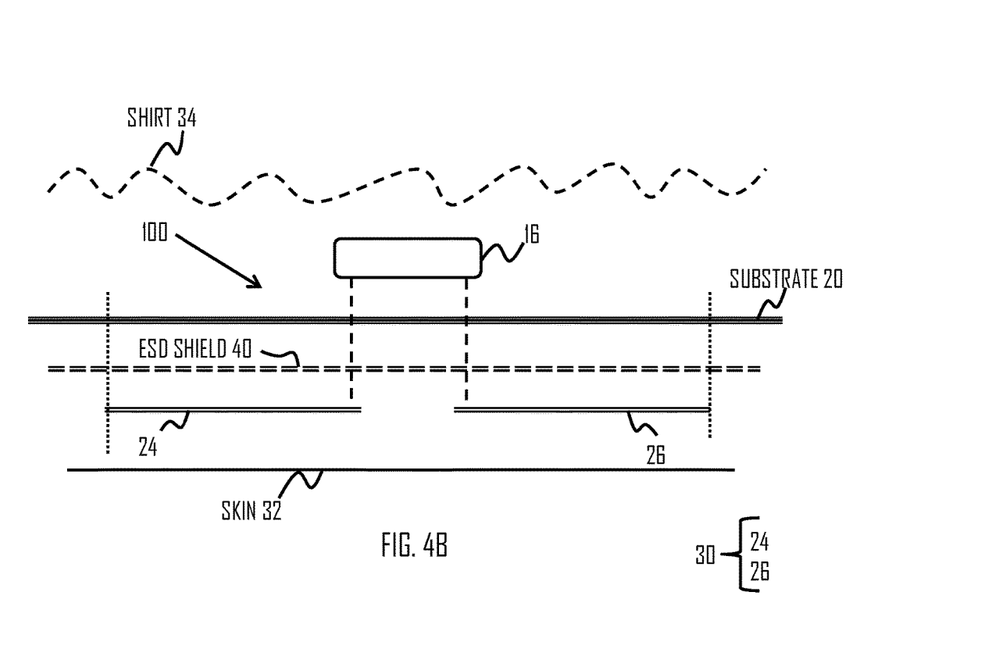

As said earlier, the environmental conditions affect the success of the heart activity measurement, which may be based on detecting millivolt-range signals on the skin 32 of the person 60. These environmental conditions may include static electricity and voltage generation from external sources, such as from the clothes or textiles of the exerciser 60. Accordingly, the heart activity sensor structure 100, as shown in FIGS. 4A and 4B, further comprises an electrostatic discharge (ESD) shield 40 applied on one side of the textile substrate 20 for protecting the at least two electrodes 24, 26 from static electricity. The intermediate insulation layer 22, the skin insulation layer 28, the instant connectors 12, 14, and other through-hole related elements shown in FIGS. 1 to 3 are not depicted in all of the Figures for reasons of simplicity. However, in an embodiment, at least some or all of the omitted elements are comprised in the various embodiments of the heart activity sensor structure 100.

Static electricity may be seen as a contrary to current electricity, which flows via wires or other conductors and transmits energy. The phenomenon of static electricity may be caused whenever two surfaces contact and separate. When two materials are in contact, electrons may move from one material to the other, which leaves an excess of positive charge on one material, and an equal negative charge on the other. When the materials are separated they retain this charge imbalance. In the field of exercising, such two surfaces may be the shirt 34 worn by the exerciser 60 and the heart activity sensor structure 100. The ESD, on other hand, denotes a sudden flow of electricity between two objects, such as the shirt 34 worn by the exerciser 60 and the heart activity sensor structure 100, and may be caused by the static electricity. The ESD may damage the heart activity sensor structure 100 or the ESD may affect the accuracy of the heart activity measurement. However, advantageously due to the application of the ESD shield 40, the possibly generated static electric charges may be conducted away from the vicinity of the electrodes 24, 26, or at least the electric charges may be spread evenly in the vicinity of the electrodes 24, 26. Such even distribution of the static electricity may be beneficial as then the skin electrodes 24, 26 have the same ambient environment and may thus detect the voltage differences on the skin 32 more accurately without being interrupted by the static electricity possibly generated on the opposite side of the electrodes 24, 26 than the skin 32.

In an embodiment, the ESD shield 40 is flexible. In an embodiment, the material of the flexible ESD shield 40 may be any conductive material, such as any metal, e.g. silver or copper. In an embodiment, the ESD shield 40 may be made of a conductive metal tape, metal film or a conductive textile arranged on the opposite side of the electrodes 24, 26 than the skin 32. Thus, the ESD shield 40 may be on the opposite side of the at least two electrodes 24, 26 than the skin 32.

The flexible ESD shield 40 may be applied on (attached to) the flexible textile substrate 20 and, more particularly, on either side of the flexible textile substrate 20. In an embodiment, the ESD shield 40 is arranged on either surface of the flexible substrate 20. Let us look at these closer with reference to FIGS. 4A and 4B. In FIG. 4A, the heart activity sensor 100 comprises at least the following plurality of layers: a first layer comprising the at least two electrodes 24, 26 and configured to be placed against the skin 32 of the exerciser 60, a second layer arranged on top of the first layer and comprising the textile substrate 20, and a third layer arranged at least partially on top of the second layer and comprising the ESD shield 40. Thus, the electrodes 24, 26, the flexible substrate 20 and the flexible ESD shield 40 form layers which may be attached on top of each other. The attachment may be obtained with tape, wire, glue, stitching, knitting, weaving, for example, to mention only a few non-limiting options. The embodiment of FIG. 4A provides ease of implementation as the attachment between the electrodes 24, 26 and the substrate 20 remains as usual. In FIG. 4B, the order of the second and third layers is switched.

In an embodiment, as shown in FIGS. 4A and 4B, the ESD shield 40 covers at least the area in which the at least two electrodes 24, 26 are located. The area in which the at least two electrodes 24, 26 are located may be defined both in length and in width of the heart activity sensor structure 100. From FIGS. 4A and 4B it may be seen that the ESD shield 40 is longer than the area in which the at least two electrodes 24, 26 are located. This is shown by the ESD shield 40 exceeding vertical dotted lines in FIGS. 4A, 4B. The length may be defined in the horizontal dimension on the surface of the skin 32 when the heart activity sensor structure 100 is worn against the chest of the exerciser 60, for example. Further, for example, in FIG. 5B it may be seen that the ESD shield 40 is wider than the area in which the at least two electrodes 24, 26 are located, as shown by the ESD shield 40 exceeding vertical dotted lines in FIG. 5B. The width may be defined in the vertical dimension on the surface of the skin 32 when the heart activity sensor structure 100 is worn against the chest of the exerciser 60, for example. In this way the ESD shield 40 may protect and cover the electrodes 24, 26 from the static electricity efficiently.

Figure 5A:
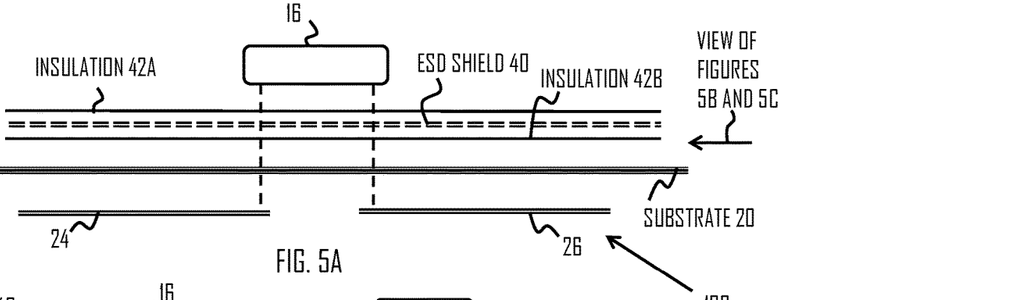
FIG. 5A shows an insulation applied to the ESD shield according to an embodiment.

In an embodiment, as shown in FIG. 5A, the flexible ESD shield 40 is electrically insulated from the textile substrate 20 and from the at least two electrodes 24, 26. This may be beneficial, for example, when the textile substrate 20 absorbs moisture during the exercise which may lead the textile substrate to become at least somewhat electrically conducting. Such electrical conduction of the textile substrate 20 may cause any non-insulated ESD shield to be in electrical contact with the skin 32 via the conductive substrate 20 in an uncontrollable manner (depending on the location of the ESD shield 40). This may cause the signal-to-noise ratio (SNR) of the ECG signal to become weaker, thus leading to poorer ECG measurement accuracy. However owing to the electrical insulation applied to the ESD shield 40 according to this embodiment, the ESD shield 40 does not become uncontrollably contacted with the skin 32, for example. Further, it may be important that the ESD shield 40 is not in electrical contact with the electrodes 24, 26. Thus, depending on the location of the ESD shield 40, an electrical insulation between the ESD shield 40 and the electrode 24, 26 (electrode layer 30) may be provided.

In an embodiment, the ESD shield 40 comprises at least one layer 42A, 42B made of an electrically non-conducting material which provides for the electrical insulation. The insulation may be obtained with a plastic or thermoplastic tape glued onto the ESD shield 40, for example. In an embodiment, in case the ESD shield 40 is on top of the flexible substrate 20, as shown in FIG. 5A, the insulation layer 42A may be omitted. However, in case the ESD shield 40 is between the flexible substrate 20 and the electrode layer 30, as is the case in FIG. 4B, there may be need to apply both of the insulation layers 42A and 42B on both sides of the ESD shield 40 in order to obtain electric insulation to the electrodes 24, 26 and also to the flexible substrate 20. The insulation layers 42A, 42B may be wider and longer than the ESD shield 40 in order to provide for efficient insulation.

In an embodiment, the ESD shield 40 is formed into a sock-like structure comprising both of the insulation layers 42A, 42B, which provides for the electric insulation from the ESD shield structure 40 to the flexible substrate 20 to the electrodes 24, 26. In the sock-like structure, the insulation layers 42A, 42B may be attached to each other at least at one end, although not shown in the Figures. In an embodiment, the insulation layers 42A, 42B are attached to each other at both ends. In an embodiment, as shown in FIG. 5B which shows a horizontal view along the skin 32 of the person 60, the insulation layers 42A, 42B are attached to each other longitudinally at sides to form the sock-like structure.

In FIGS. 4A to 5C, dashed lines show how the electrical connection between the electrodes 24, 26 and the electronics module 16 is provided. The electrical connection, such as an electrically conducting wire, may penetrate the flexible textile substrate 20, the ESD shield 40 and/or the insulation layer(s) 42A, 42B. The penetration may be provided with through-holes in the flexible textile substrate 20, in the ESD shield 40 and/or in the insulation layer(s) 42A, 42B. The through-holes may be electrically insulated from the corresponding layer to which they are formed, e.g. from the flexible textile substrate 20, the ESD shield 40 and/or the insulation layer(s) 42A, 42B. This may be beneficial so as to conduct the measured ECG signals only to the electronics module 16 and not to the layers of the heart activity sensor structure 100.

Figure 5B:
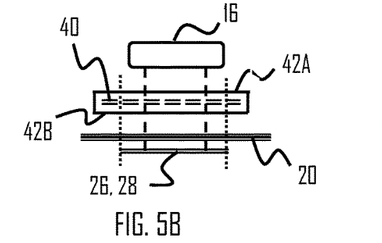
FIGS. 5B and 5C illustrate electrical connection between electrodes and an electronics module according to some embodiments.
Figure 5C:
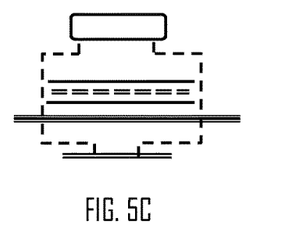

For example, looking horizontally along the skin 32 of the person 60, FIG. 5B shows how the electrical connection penetrates the flexible textile substrate 20, the ESD shield 40 and the insulation layer(s) 42A, 42B. However, FIG. 5C shows how the electrical connection, such as a wire, may be arranged to circulate the ESD shield 40 and the insulation layer(s) 42A, 42B from the sides (an upper side and a lower side when the heart activity sensor structure 100 is worn on the chest of the exerciser 60). This may be beneficial to avoid implementing through-holes in the ESD shield 40 and in the insulation layer(s) 42A, 42B. It should be noted that the electrical connection, such as wires, may travel at least partly inside the flexible substrate 20 to which the electrodes 24, 26 may be mounted.

Figures 6A, 6B:
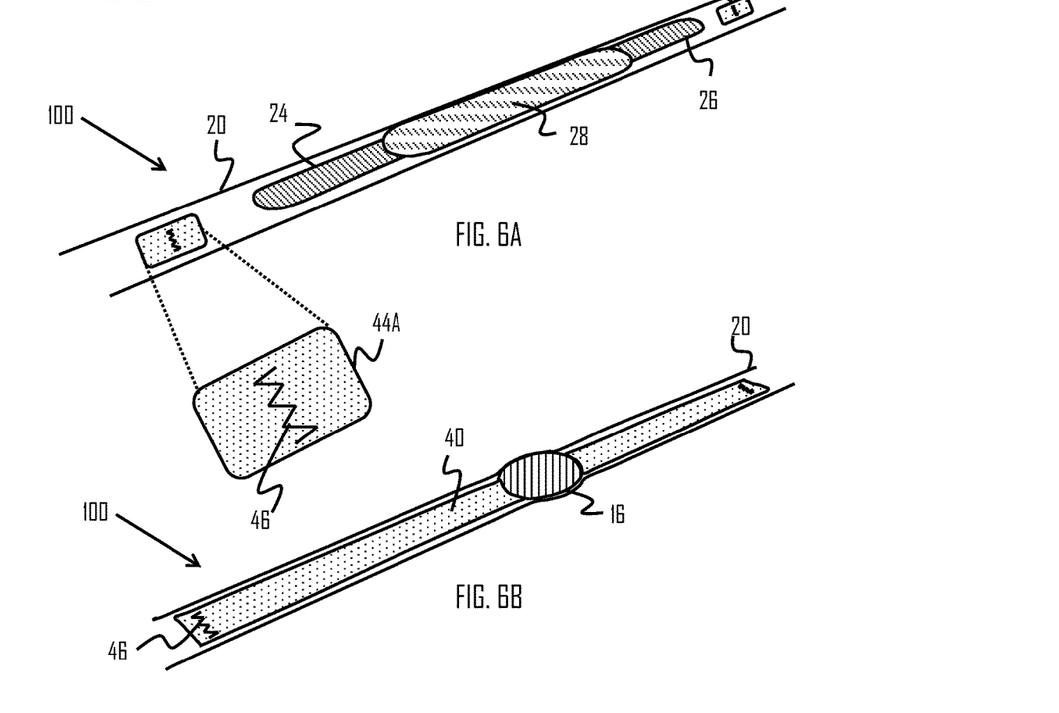
FIGS. 6A and 6B depict grounding elements according to an embodiment.

In an embodiment, the heart activity sensor structure 100 further comprises, as shown in FIGS. 6A and 6B, at least one grounding element 44A, 44B coupled to the ESD shield 40 and configured to contact the skin 32 of the exerciser 60 during use. This at least one grounding element 44A, 44B provides for grounding of the ESD shield 40 to the skin 32 and therefore acts as a gateway for the static electricity to pass to the skin 32 which may be seen as an electrical ground. FIG. 6A shows the heart activity sensor structure 100 from the side which is against the skin 32 of the exerciser 60 during use, whereas FIG. 6B shows an opposite (top) view of the heart activity sensor structure 100. In these Figures, it is assumed that the ESD shield 40 is placed on top of the flexible textile substrate 20. The grounding element(s) 44A, 44B may be made of any conducting material.

In an embodiment, at least one location in which the at least one grounding element 44A, 44B contacts the skin is at the at least one end of the flexible textile substrate 20. However, in order to provide more efficient grounding, in an embodiment, there are two grounding elements 44A, 44B, one at each end of the flexible textile substrate 20. An end of the flexible textile substrate 20 may be defined as an area between the longitudinal end of the flexible textile substrate 20 and the electrode 24 or 26 on the respective longitudinal side of the flexible textile substrate. In case there exists at least one insulation layer 42A, 42B, there may be a through-hole in the respective insulation layer(s) 42A, 42B, through which the ESD shield 40 may be connected to the at least one grounding element 44A, 44B.

In an embodiment, the heart activity sensor structure 100 further comprises a conducting string structure 46 for coupling the at least one grounding element 44A, 44B and the ESD shield 40, wherein the conducting string structure 46 penetrates the textile substrate 20. As shown in FIGS. 6A and 6B, the ESD shield 40 may be on top of the textile substrate 20 whereas the electrode layer 30 (comprising electrodes 24, 26) is on the opposite side of the textile substrate 20. In such case, the conducting string structure 46 may provide a reliable and cost-efficient manner of electrically coupling the ESD shield 40 to the grounding element(s) 44A, 44B. The string structure 46 may be, for example, a metal string attached (e.g. knitted, woven) to the ESD shield 40 and to the respective grounding element 44A, 44B. For example, from the point of view of manufacturing the heart activity sensor structure 100, the string structure 46 may be easily added (e.g. knitted, woven) to the heart activity sensor structure 100 without having to make any special through-holes or a like in the flexible textile substrate 20. Similarly, the string structure 46 may penetrate the insulating layer 42B, if such is used.

In the case both the electrode layer 30 and the ESD shield 40 are on the same side of the flexible textile substrate 20 (not shown in FIGS. 6A, 6B), the grounding element(s) 44A, 44B may be directly attached to the ESD shield 40. In an embodiment referring to such order of the layers, there may be hole(s) in the insulation layer 42B which allow the ESD shield 40 to contact the skin 32 during use. In this embodiment, the portion(s) of the ESD shield 40 touching the skin 32 may be seen as the grounding element(s) 44A, 44B. In yet one embodiment referring to such order of the layers, the grounding element(s) 44A, 44B may be also in this case connected to the ESD shield 40 via the conducting string structure 46 penetrating the insulation layer 44B, if such exists. It should be noted that the intermediate insulation layer 22 of FIG. 3 may provide for the insulation between the electrodes 24, 26 and the ESD shield 40, instead of the insulation layer 44B. In such case, if the ESD shield is longer than the intermediate insulation layer 22, the portion(s) of the ESD shield 40 extending further than the intermediate insulation layer 22 may be seen as the grounding element(s) 44A, 44B contacting the skin 32 of the exerciser 60.

In an embodiment, the heart activity sensor structure 100 comprises an electronics module 16 configured at least to transmit information related to the heart activity to the training computer 16, as indicated with reference to FIGS. 1A and 1B. The electronics module 16 may further comprise also other functional entities than the transmitter, as described earlier.

Figure 7A:
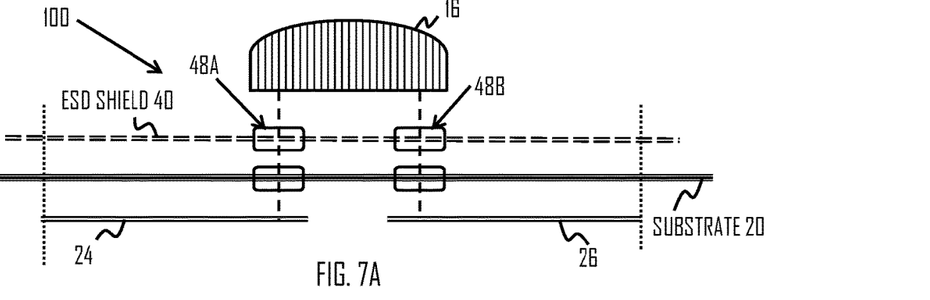
FIGS. 7A, 7B, and 7C illustrate mounting of the electronics module according to some embodiments.

In an embodiment, as shown in FIG. 7A, the electronics module 16 is detachably coupled to the at least two electrodes 24, 26. In this case, there may be the press studs 12, 14 or other electromechanical connectors which provide for the attaching and detaching of the electronics module 16 to/from the substrate 20. Further, in this case the ESD shield 40 may comprise at least one through-hole 48A, 48B in order to allow the electrical coupling between the at least two electrodes 24, 26 and the electronics module 16 to pass the ESD shield 40. As said, also the substrate 20 may comprise through-holes for allowing the electrical connection to pass. The through-holes may be electrically insulated from the layer to which they are formed.

Figure 7B:
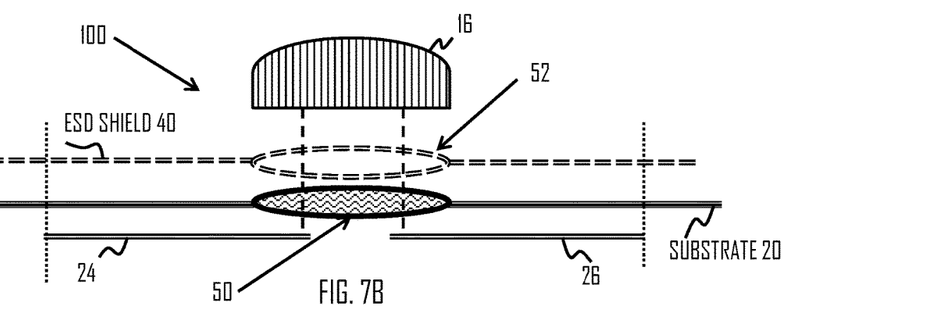
Figure 7C:
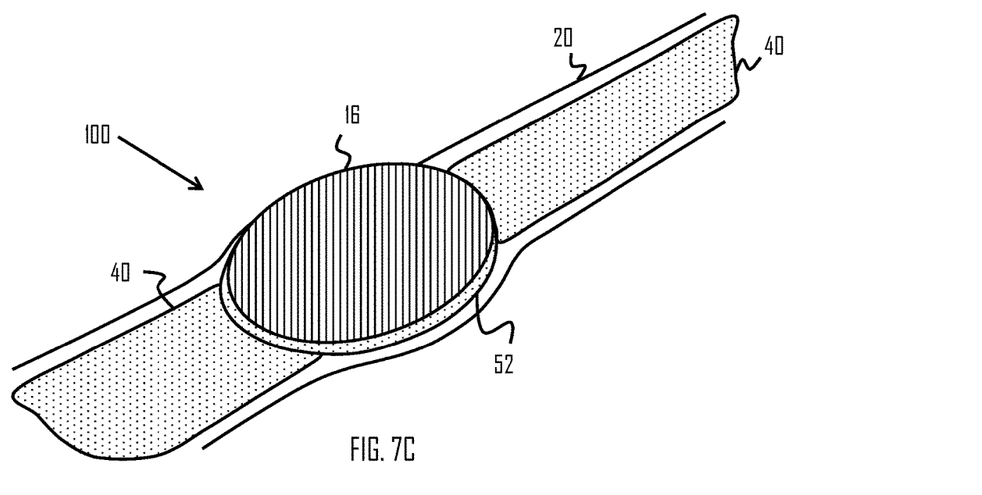

However, in an embodiment, the electronics module 16 is integrated (non-detachably) as part of the heart activity sensor structure 100. In this case, the electronics module 16 is, as shown in FIGS. 7B and 7C, mounted integrally to a base 50 of the substrate 20. In an embodiment, the base 50 may be an engraving in the substrate 20, wherein the dimensions of the engraving may be appropriate to fit the electronics module 16. In another embodiment, the base 50 may be a location on the surface of the substrate 20 to which the electronics module 16 is mounted to. The attachment between the electronics module 16 and the base 50 may be obtained with glue, for example. The base 50 and the electronics module 16 may comprise electrical connecting elements which provide for electrical connection between the electronics module 16 and the electrodes 24, 26.

In an embodiment, the heart activity sensor structure 100 comprises a first part of the ESD 40 on one side of the electronics module 16 and a second part of the ESD 40 on the other side of the electronics module 16. The first and second parts may be electrically separated from each other. However, in an embodiment, the electronics module 16 comprises a conducting structure configured to electrically connect the first part and the second part with each other. Such conducting structure may, e.g. in a casing that covers the electronics module 16.

Figure 8:
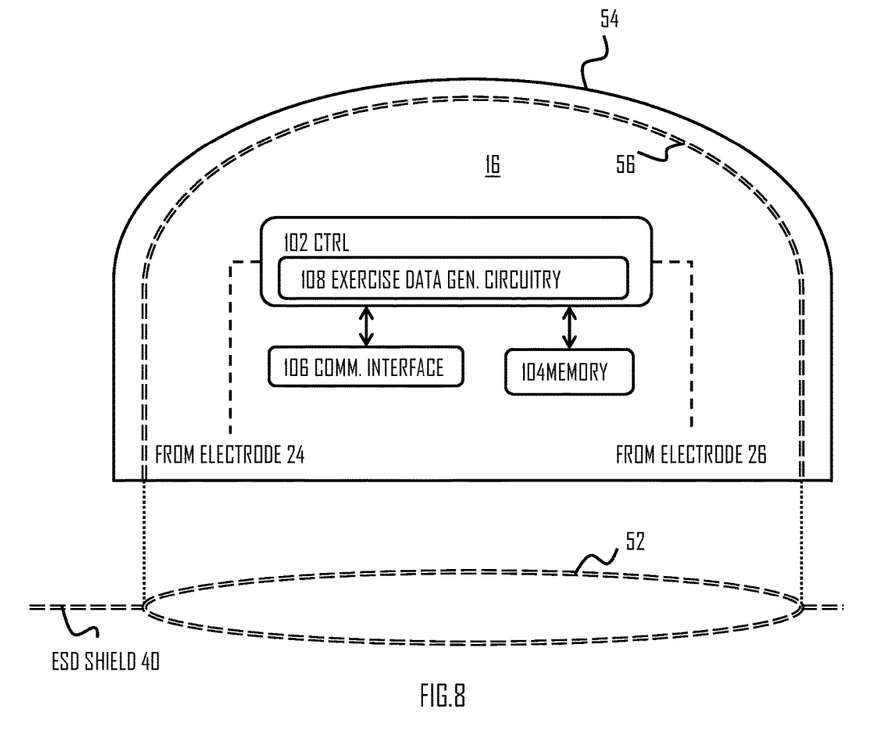
FIG. 8 shows the electronic module according to an embodiment.

In an embodiment, the heart activity sensor structure 100 and, more particularly, the base 50 comprises electrically conducting periphery element 52 coupled to the ESD shield

40, as shown in FIGS. 7B, 7C and 8. The periphery element 52 may be in the form of a ring, an ellipse or a rectangular, to mention only a few possibly non-limiting options. The shape of the periphery element 52 may depend on the shape of the base 50, for example. Thus, the ESD shield 40 may advantageously be a continuous element in front of the electrodes 24, 26. As shown, the periphery element 52 may be electrically connected to the ESD shield 40, thus forming part of the ESD shield 40.

In an embodiment, as shown in FIG. 8, the electronics module 16 comprises a casing covering the electronics module 16. The casing may comprise an electrically non-conductive outer surface 54 and electrically conductive inner film 56. The electrically non-conductive outer surface 54, which may be of plastic, may be beneficial so as no electric shocks are passed to the exerciser 60 touching the electronics module 16.

There may be static electricity generated in the electronics module 16 due to the movement of the shirt 34 against the module 16, for example. Thus, in such case, the electrically conductive inner film 56 may be of importance in protecting the electronic components of the electronic module 16 from the ESD of the static electricity. Accordingly, in an embodiment, the electrically conductive inner film 56 may be electrically coupled to the ESD shield 40. This may take place either directly or via the periphery element 52 of the base 50. In the latter case, the electrically conducting periphery element 52 may be coupled to the electrically conductive inner film 56 of the electronics module 16, as shown in FIG. 8. As a result, the inner film 56 may form part of the (continuous) ESD shield 40. This may provide protection for the electronic components inside the electronics module 16 and also provide more efficient shielding of the electrodes 24, 26.

In an embodiment, the surface of the base 50 is electrically conductive and acts as part of the ESD shield 40. There may be electric insulations applied in required portions of the base in order to ensure that, for example, the electrical connection between the module 16 and the electrodes 24, 26 is not affected by the ESD shield 40.

In an embodiment, the surface of the base 50 is electrically conductive and the electronics module 16 comprises the electrically conductive inner film 56, and these electrically conductive portions are coupled to each other. This embodiment may create a Faraday's cage or shield for the electronics module 16, thus protecting it from static electricity efficiently.

It should be noted that FIGS. 4A to 5C, 7A, 7B, and 8 are explosion Figures. Thus, it is clear that although the layers/components in the Figures are drawn separated from each other, the layers/components may be attached layer wise on top of each other to form the heart activity sensor structure 100. In an embodiment, the ESD shield 40 is at least partially inside the flexible textile substrate 20.

As shown in FIG. 8, the electronics module 16 may comprise a control circuitry (CTRL) 102, such as at least one processor, and at least one memory 104 including a computer program code, wherein the at least one memory 104 and the computer program code, are configured, with the at least one processor 104, to cause the electronics module 16 to carry out a specific task with respect to the detected ECG signal, for example. The memory 104 may be implemented using any suitable data storage technology, such as semiconductor based memory devices, flash memory, magnetic memory devices and systems, optical memory devices and systems, fixed memory and removable memory.

The control circuitry 102 may comprise an exercise data generation circuitry 108 for generating the exercise data related to the detected ECG signals. The generated data may represent, for example, heart rate or heart rate variation. The apparatus may further comprise communication interface 106 comprising hardware and/or software for realizing communication connectivity according to one or more communication protocols, such as Bluetooth, Bluetooth Smart, wireless local area network (WLAN, WiFi), infrared (IR), wireless communication utilizing electric and/or magnetic fields, ANT, ANT+, or WIND. The communication connection may be applied for transmitting exercise data to the training computer 17 or to receive data from the training computer 17, for example.

Figure 9:
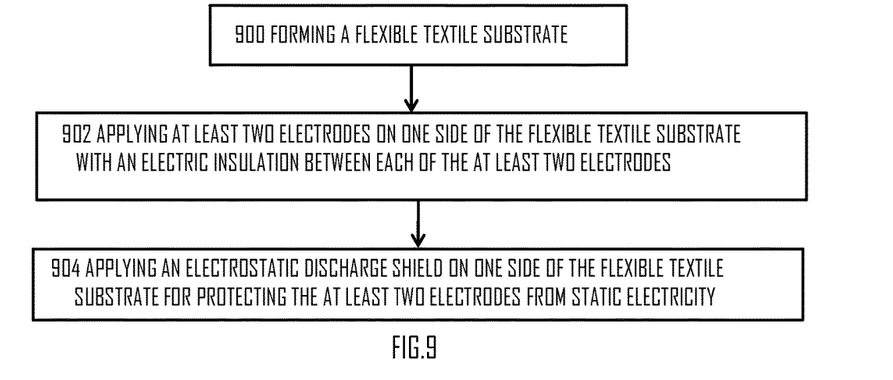
FIG. 9 illustrates a method according to an embodiment.

There is also provided a method, as shown in FIG. 9, comprising, in step 900, forming a flexible textile substrate. In step 902, the method comprises applying at least two electrodes 24, 26 on one side of the flexible textile substrate 20 with an electric insulation between each of the at least two electrodes 24, 26, wherein the at least two electrodes 24, 26 are configured to be placed against a skin 32 of an exerciser 60 in order to measure biosignals related to heart activity. In step 904, the method comprises applying an electrostatic discharge shield 40 on one side of the flexible textile substrate 20 for protecting the at least two electrodes 24, 26 from static electricity.

It may be possible that the heart activity sensor structure comprises parts that have been printed using an electronics printing technique. The electronics printing technique may be a technique where electronics are printed, using ink- or paste-like materials, on a substrate. The ink may comprise, for example, carbon-based compounds.

In an embodiment, the exerciser 60 is a user of the heart activity sensor structure. Therefore, although embodiment(s) may be described in relation to physical exercise performed by the exerciser 60, it may be equally possible that the heart activity sensor structure is used by the user. Thus, the heart activity sensor structure may be further used in everyday situations that are not necessarily related to physical exercise. For example, the heart activity sensor structure may be used when sleeping, during work day, walking, sitting and/or driving, to name a few examples.

Figure 10A:
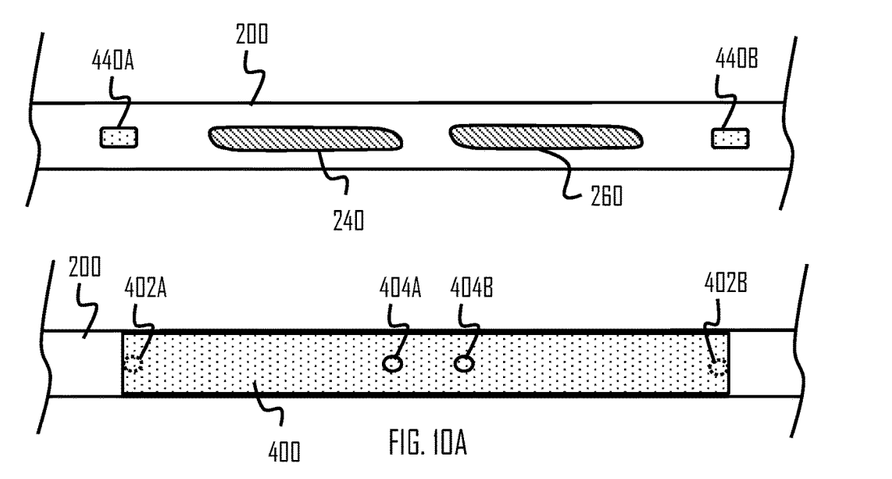

In an embodiment, as shown in FIG. 10A, the heart activity sensor structure is illustrated from one side, and an opposite side, respectfully. Said one side may be the upper image, and the opposite side may be the lower image. The heart activity sensor may comprise a flexible substrate 200 being substantially non-conducting. The flexible substrate 200 may comprise and/or be made of polymer(s), such as Thermoplastic Polyurethane (TBU) and/or elastic material(s), such as rubber or similar. In an embodiment, the flexible substrate 200 comprises the flexible textile substrate 20, or vice versa. In an embodiment, the flexible substrate 200 is made of non-conductive material(s), or at least comprises non-conductive material(s).

The flexible substrate 200 may comprise such material(s) (listed above) which may prevent dampness from effecting substantially the heart activity measurement. Further, the elasticity and/or flexibility of the flexible substrate 200 may decrease on the areas where printing is performed. In other words, the flexible substrate 200 may become stiffer on areas where electronics are printed. This may benefit the heart activity measurement, as the printed components may then be more robust against external forces.

Referring to FIG. 10A, the heart activity sensor structure may further comprise at least two electrodes 240, 260, wherein the at least two electrodes 240, 260 are printed on one side of the flexible substrate 200 and configured to be placed against the skin 32 of the exerciser 60 in order to measure biometric signals related to heart activity. The at least two electrodes 240, 260 may comprise silicon-based material, conductive TBU and/or some other polymer(s), that have been printed on the flexible substrate 200. Naturally, the materials used may be at least partially conductive in order to the at least two electrodes 240, 260 to function properly. It may be also possible to use material compounds comprising metal(s) for the printing. This may require heating the metallic material compound in order to get it bond with the flexible substrate 200 in the printing process.

Using silicon-based material for the printing may enhance the gripping ability of the at least two electrodes 240, 260 against the skin 32 of the exerciser 60, or a user of the heart activity sensor structure. Enhanced gripping ability may enhance the heart activity measurement as the at least two electrodes 240, 260 may be more steadily in contact with the skin 32. Further, silicon-based material may have an ability to keep carbon particles in form over time, and thus better retain its ability to conduct electricity. This may be beneficial as operating life of the heart activity measurement sensor may be enhanced.

In an embodiment, the at least two electrodes 24, 26 comprise and/or are the printed at least two electrodes 240, 260.

Further, the heart activity sensor structure may comprise an electrostatic discharge shield 400 printed on opposite side of the flexible substrate 200, compared to the printing of the at least two electrodes 240, 260, for protecting the at least two electrodes 240, 260 from the static electricity. The electrostatic discharge shield 400 may be printed using similar materials as the at least two electrodes 240, 260, for example. The electrostatic discharge shield 400 may prevent and/or limit harmful electricity from reaching the at least two electrodes 240, 260.

In an embodiment, the electrostatic discharge shield 400 is printed on the flexible substrate 200, wherein the electrostatic discharge shield 400 is printed on an opposite side of the flexible substrate in relation to the printing of said electrodes, and wherein the electrostatic discharge shield is for protecting the at least two electrodes from static electricity.

In an embodiment, the electrostatic discharge shield 40 comprises and/or is the printed electrostatic discharge shield 400.

In an embodiment, the heart activity sensor structure comprises at least the following plurality of layers: a first layer comprising the printed at least two electrodes 240, 260 and configured to be placed against the skin 32 of the exerciser 60, a second layer arranged on top of the first layer and comprising the flexible substrate 200, and a third layer arranged at least partially on top of the second layer and comprising the printed electrostatic discharge shield 400.

Still referring to FIG. 10A, the electrostatic discharge shield 400 may cover at least an area, on the opposite side of the flexible substrate 200, on which the at least two electrodes 240, 260 are located. This may mean that the opposite side of the flexible substrate 200 may be covered from the areas on which the at least two electrodes 240, 260 are situated. This may be beneficial, as the static electricity may be then at least more evenly spread among the at least two electrodes 240, 260 and/or the static electricity may be conducted away from the areas on which the at least two electrodes 240, 260 are situated.

Further, the flexible substrate 200 may itself prevent static electricity from reaching the at least two electrodes 240, 260, as the flexible substrate may be non-conductive. However, the amount of electrostatic energy may reach a certain threshold, and thus possibly cause an electric breakdown. Therefore, using the electrostatic discharge shield 400 may be beneficial, as the amount of electrostatic energy may be controlled, and even further conducted away from the area of the at least two electrodes 240, 260.

In an embodiment, the heart activity sensor structure comprises: at least one grounding element 440A, 440B printed, on the same side of the flexible substrate 200 as the at least two measuring electrodes 240, 260, electrically coupled to the electrostatic discharge shield 400 and configured to contact the skin 32 of the exerciser 60. The at least one grounding element 440A, 440B may comprise similar materials as the at least two electrodes 240, 260, for example. In an embodiment, the at least one grounding element 440A, 440B comprises at least one electrode, wherein the at least one electrode is adapted to conduct electricity from the electrostatic discharge shield 400 to the skin 32.

In an embodiment, the at least one grounding element 44A, 44B comprises and/or is the printed at least one grounding element 440A, 440B.

In an embodiment, the at least one grounding element 440A, 440B is printed on the same side as the electrostatic discharge shield 400. In such case the flexible substrate may be bended, when in use, to allow to the at least one grounding element 440A, 440B to contact skin 32 of the exerciser 60. In another embodiment, the at least one grounding element 440A, 440B may not be in contact with the skin 32. In such case, the at least one grounding element 440A, 440B may be in contact, for example, with clothes of the exerciser 60, thus conducting electrostatic energy away from the measuring area. For example, exerciser's clothes may comprise parts which are substantially in ground potential. These area(s) may be coupled with the at least one grounding element 440A, 440B, for example. For example, the clothes may be in ground potential as they may become wet during training, and thus be electrically conducting, and be in contact with the skin 32 of the user. However, dampness of the clothes (caused by, for example, sweat) may not be necessarily required, as the fibers in the clothes may comprise conductive material(s).

In an embodiment, the at least one grounding element 440A, 440B is printed at a distance from the at least two electrodes 240, 260. The distance may be, for example, 1 centimeter, 5 centimeters or 10 centimeters, to name a few examples. Printing the at least one grounding element 440A, 440B at the distance from the at least two electrodes 240, 260 may mean that the electricity conducted by the grounding element(s) may not interfere with the heart activity measurement, and more specifically, the at least two electrodes 240, 260.

In an embodiment, the at least one grounding element 440A, 440B is configured to conduct electrostatic discharges away from measuring areas of the at least two electrodes 240, 260. Similar to the previous embodiment, this may bring the benefit of reducing the interference, of the electrostatic discharges, to the heart activity measurement.

In an embodiment, at least one location in which the at least one grounding element 440A, 440B is configured to contact the skin 32 is at the at least one end of the flexible substrate 200. For example, if the flexible substrate 200 is used to attach the heart activity sensor structure around the exerciser 60, such as around the exerciser's 60 body, wrist, leg and/or head, the at least one end of the flexible substrate 200 may be situated, when in use, on opposite side of the exerciser 60 compared to the at least two electrodes 240, 260. Thus, it may be beneficial to conduct the electrostatic discharges as far away, from the measuring area of the at least two electrodes 240, 260, as possible.

In an embodiment, the electrostatic discharge shield 400 covers the area, on the opposite side of the flexible substrate 200, on which the at least one grounding element 440A, 440B is located. For example, if the at least one grounding element 440A, 440B is located at least one end of the flexible substrate 200, the electrostatic discharge shield 400 may reach to that area on the opposite side of the flexible substrate.

In an embodiment, the at least one grounding element 440A, 440B comprises two or more grounding elements 440A, 440B printed on the flexible substrate 200. The two or more grounding elements 440A, 440B may be printed so that the at least two electrodes 240, 260 are located substantially between the two or more grounding elements 440A, 440B. As shown in FIG. 10A, one grounding element 440A may be on the right side and another grounding element 440B maybe on the left side compared to the at least two electrodes 240, 260. In an embodiment, the at least one grounding element 440A, 440B is situated between the at least two electrodes 240, 260.

Still referring to FIG. 10A, the flexible substrate 200 may comprise at least one through-hole 402A, 402B, and corresponding at least one lead-through printed to the flexible substrate 200, wherein the at least one lead-through enables electrical coupling between the at least one grounding element 440A, 440B and the electrostatic discharge shield 400. As described above, the grounding element(s) 440A, 440B and the electrostatic discharge shield 400 may be printed on an opposite sides of the flexible substrate 200. Therefore, the electrical coupling between said element(s) and shield may be achieved, for example, by using the described at least one through-hole 402A, 402B and the corresponding at least one lead-through.

The at least one through-hole 402A, 402B may be situated at least partially on same area(s) as the at least one grounding element 440A, 440B. Thus, the at least one lead-through may be in contact with the at least one grounding element 440A, 440B. The printing material of the at least one lead-through may be similar to that of, for example, at least one grounding element 440A, 440B, at least two electrodes 240, 260 and/or electrostatic discharge shield 400. The at least one lead-through may comprise electrically conductive material.

Further, the at least one through-hole 402A, 402B may be situated at least partially on same area(s) as the electrostatic discharge shield 400. Naturally, this may mean that the at least one through-hole extends from one side to the opposite side of the electrostatic discharge shield 400.

In an embodiment, the at least one lead-through is printed on both sides of the flexible substrate 200, wherein the both sides are the sides comprising the electrostatic discharge shield 400 and the at least one grounding element 440A, 440B, respectfully.

In an embodiment, the at least one lead-through is printed on one side of the flexible substrate 200. Thus, the printing material, such as polymer, may penetrate the at least one through-hole 402A, 402B from one side to the opposite side of the flexible substrate 200.

In one example, as shown in FIG. 10A, the at least one through-hole 402A, 402B may be situated on areas of ends of the electrostatic discharge shield 400. This may be beneficial, as the distance between the grounding element(s) 440A, 440B and the at least one electrode 240, 260 may determine how long the electrostatic discharge shield 400 should be. In other words, it may be beneficial to print the electrostatic discharge shield 400 so that it just reaches the at least one grounding element 440A, 440B when the coupling between the two is made using the lead-through(s). This may save printing material.

In an embodiment, the electrostatic discharge shield 400 is located on top of the at least one through-hole 402A, 402B. Thus, the at least one through-hole 402A, 402B shown in FIG. 10A may be located under the electrostatic shield 400.

In an embodiment, the at least one grounding element 440A, 440B is located on top of the at least one through-hole 402A, 402B.

In an embodiment, the heart activity sensor structure comprises a connection module for electrically coupling the electronics module 16 with the at least two electrodes 240, 260, wherein the connection module is electrically coupled with the at least two electrodes 240, 260. The connection module may comprise, for example, snap fastener(s). In an embodiment, the connection module comprises a base dimensioned and adapted to mount the electronics module 16 to the heart activity sensor. The connection module may be arranged on top of the electrostatic discharge shield 400, for example.

In an embodiment, the base comprised in the connection module is adapted and dimensioned to allow detachably mounting the electronics module 16 to the heart activity sensor structure.

In an embodiment, the electronics module 16 is configured at least to transmit information related to the heart activity to the training computer 17.

In an embodiment, the electronics module 16 is integrated as part of the heart activity sensor structure. Thus, at least some parts of the electronics module 16 may be printed on the flexible substrate 200, on the connection module and/or the electrostatic discharge shield 400.

In an embodiment, the connection module is at least partially printed on the electrostatic discharge shield 400 and/or the flexible substrate 200.

In an embodiment, the flexible substrate 200 and the electrostatic discharge shield 400 comprise at least one through-hole 404A, 404B, and corresponding at least one lead-through printed to at least one of the flexible substrate 200, electrostatic discharge shield 400, and wherein said at least one lead-through enables electrical coupling between the at least two electrodes 240, 260 and the connection module. As the connection module may be situated on top of the electrostatic discharge shield 400, the at least one through-hole 404A, 404B may need to reach through the flexible substrate 200 and the electrostatic discharge shield 400 in order to enable the electrical connection. Naturally, described connection may be used to connect the electronics module 16 to the at least two electrodes 240, 260. The printing material(s) and/or methods may be similar for said lead-through(s) as for the lead-through(s) described in relation to the at least one grounding element 440A, 440B.

Figure 10B:
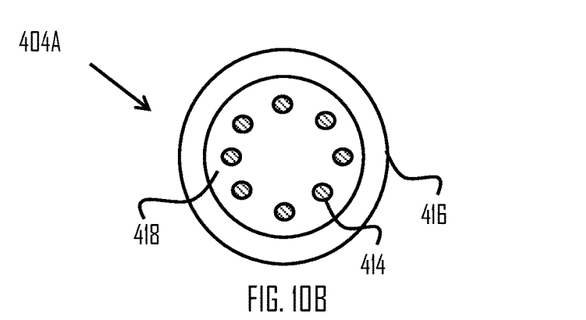
Figure 10C:
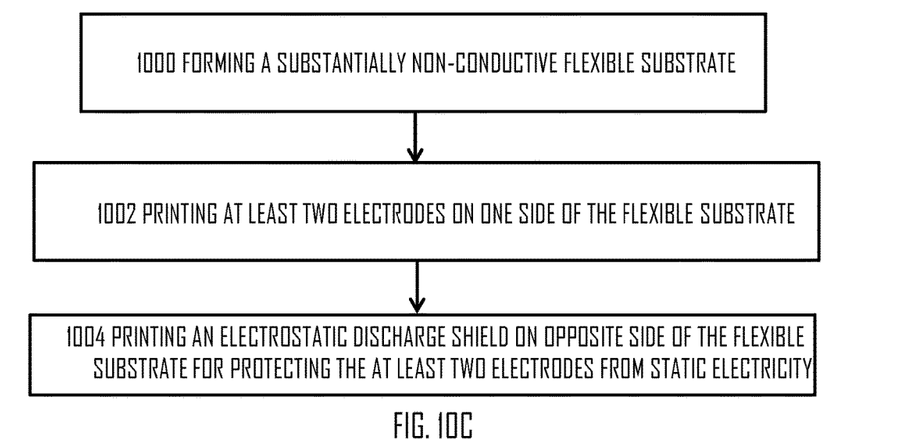

Further, it needs to be noted that the at least one through-hole 404A, 404B and the corresponding printed at least one lead-through may be electrically insulated so that only the connection points of the at least two electrodes and the connection module may be electrically connected. Thus, the electrostatic discharge shield may not be in electrical contact with said at least one lead-through due to the electrical insulation. The electrical insulation may be achieved, for example, with the at least one through-hole 404A, 404B, as it may be dimensioned and adapted so that the lead-through(s) may not touch the outer surfaces of the at least one through-hole 404A, 404B. Such example is shown in FIG. 10B. The example of FIG. 10B may be used with through-holes(s) 402A, 402B, 404A, 404B and the corresponding lead-trough(s).

Referring to FIG. 10B, the example is illustrated with the through-hole 404A and the corresponding lead-through. The lead-through may be achieved using one or more printed conductive areas 414 extending from the beginning of the through-hole to the end of the lead-through. The one or more printed conductive areas 414 may be electrically insulated from the edges of the through-hole 416. This may be achieved by using a non-conductive material in area 418 and/or area 416. Thus, the lead-through may comprise electrically non-conductive material isolating the lead-through from the material(s) to which the through-hole is made and/or pressed. This way the electricity may be conducted only to beneficial area(s).

In an embodiment, the non-conductive material of the lead-through(s) is printed to the heart activity sensor structure.

In an embodiment, the heart activity sensor structure further comprises a non-conductive layer on top of the electrostatic discharge shield. In such case, the through-hole(s) 404A, 404B and the corresponding lead-through(s) may extend through said non-conductive layer. Further, the connection module may be situated on top of said non-conductive layer.

In an embodiment, the at least one grounding element 440A, 440B has a larger resistivity compared to each of the at least two electrode(s) 240, 260. The resistivity may be substantially larger, and thus the electricity conducting ability may be substantially weaker. For example, the at least one grounding element 440A, 440B may have around 100 times larger resistivity compared to each of the at least two electrode(s) 240, 260. The resistance differences may be achieved, for example, using different printing material(s). For example, for the at least one grounding element 440A, 440B it may be possible to use compound which comprises polymer(s) with higher resistivity.

In an embodiment, the electrostatic discharge shield 400 is, at least partly, printed on the same side of the flexible substrate 200 as the at least two electrodes 240, 260. For example, the electrostatic discharge shield 400 may comprise two parts, wherein one is printed, as described in relation to FIG. 10A, and the other part is printed on the same side of the flexible substrate 200 as the at least two electrodes 240, 260. This may provide further protection against the static electricity. The at least two electrodes 240, 260 may be electrically insulated from the electrostatic discharge shield 400. One insulator may be the flexible substrate 200, but the heart activity sensor structure may comprise further layer(s) to, for example, electrically insulate the at least two electrodes 240, 260 from said other part of the electronic discharge shield 400. The heart activity sensor structure may comprise necessary through-hole(s) and corresponding lead-through(s) in order to electrically couple said two parts together. Further, said other part may be electrically coupled with the at least one grounding element 440A, 440B.

In an embodiment, the at least two electrodes 240, 260 are electrically insulated from each other.

There is provided a method for manufacturing the heart activity sensor structure, as shown in FIG. 100, the method comprising forming the substantially non-conductive flexible substrate 200 (step 1000), printing, using an electronics printing technique, the at least two electrodes 240, 260 on one side of the flexible substrate 200, wherein the at least two electrodes 240, 260 are configured to be placed against the skin 32 of the exerciser 60 in order to measure biometric signals related to heart activity (step 1010), and printing the electrostatic discharge shield 400 on the flexible substrate 200, wherein the electrostatic discharge shield 400 is printed on an opposite side of the flexible substrate 200 in relation to the printing of said electrodes 240, 260, and wherein the electrostatic discharge shield is for protecting the at least two electrodes 240, 260 from static electricity (step 1020).

In an embodiment, the method described in relation to FIG. 100 further comprises printing the at least one grounding element 440A, 440B on the same side of the flexible substrate 200 as the at least two measuring electrodes 240, 260, wherein the at least one grounding element 440A, 440B is electrically coupled to the electrostatic discharge shield 400 and configured to contact the skin 32 of the exerciser 60.

In an embodiment, the method described in relation to FIG. 100 further comprises pressing at least one through-hole 402A, 402B, 404A, 404B to at least one of the flexible substrate 200, the electrostatic discharge shield 400.

In an embodiment, the method described in relation to FIG. 100 further comprises printing at least one lead-through corresponding to the at least one through-hole 402A, 402B, 404A, 404B, wherein the at least one lead through is printed on at least one of the flexible substrate 200, the electrostatic shield 400.

In an embodiment, the printing (e.g. electronics printing) on the flexible substrate 200 comprises: first printing on one side of the flexible substrate 200, and second printing on an opposite side of the flexible substrate 200. It may be possible to first print the at least two electrodes 240, 260 and/or the electronics discharge shield 400, for example. Similarly, the lead-through(s) may be printed first on one side of the heart activity sensor structure, and then on the other side of said structure. As said, the lead-through(s) may reach from one part of the heart activity sensor structure through to another part of the heart activity sensor structure.

In an embodiment, the printing (e.g. electronics printing) on the flexible substrate 200 comprises using a vacuum or low pressure printer. This may enable the printing of components only from one side of the printing platform, such as the flexible substrate. Similarly, the lead-through(s) may be printed from one side, wherein the vacuum is used to get the printing material to the wanted other side and/or other part of the heart activity sensor structure.

Further, in relation to FIGS. 10A and 100, it may be possible to manufacture at least some of the parts of the heart activity sensor structure using a Physical Vapor Deposition (PVD) technique. For example, the at least two electrodes 240, 260 may be manufactured and/or printed using the PVD technique. As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

Some of the functionalities performed by the electronics module 16 embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A heart activity sensor structure, comprising:
    a first layer comprising at least two printed electrodes on one side of a flexible substrate, the first layer being printed, the at least two printed electrodes being configured to be placed against a skin of a user in order to measure biometric signals related to heart activity;
    a second layer comprising the flexible substrate, the flexible substrate being substantially non-conducting;
    a third layer comprising a printed electrostatic discharge shield on an opposite side of the flexible substrate in relation to the at least two printed electrodes, the third layer being printed, the printed electrostatic discharge shield protecting the at least two printed electrodes from static electricity;
    an insulation encompassing the third layer, the insulation comprising an electrically non-conducting material that provides electrical insulation between the second layer and the third layer;
    at least two through holes in the second layer, the third layer, and the insulation; and
    one or more insulated conductors coupling to the electrodes through each of the at least two through holes.

2. The heart activity sensor structure of claim 1, wherein the second layer is arranged on top of the first layer and the third layer is arranged on top of the second layer.

3. The heart activity sensor structure of claim 1, wherein the printed electrostatic discharge shield covers at least an area, on the opposite side of the flexible substrate, on which the at least two printed electrodes are located.

4. The heart activity sensor structure of claim 1, further comprising at least one printed grounding element on a same side of the flexible substrate as the at least two printed electrodes, the at least one printed grounding element being electrically coupled, by printed electrical connection, to the printed electrostatic discharge shield and configured to contact the skin of the user.

5. The heart activity sensor structure of claim 4, wherein the at least one printed grounding element is printed at a distance from the at least two printed electrodes.

6. The heart activity sensor structure of claim 4, wherein the at least one printed grounding element is configured to conduct electrostatic discharges away from measuring areas of the at least two printed electrodes.

7. The heart activity sensor structure of claim 4, wherein at least one location in which the at least one printed grounding element is configured to contact the skin is at the at least one end of the flexible substrate.

8. The heart activity sensor structure of claim 4, wherein the printed electrostatic discharge shield covers an area, on the opposite side of the flexible substrate, on which the at least one printed grounding element is located.

9. The heart activity sensor structure of claim 4, wherein the at least one printed grounding element comprises two or more printed grounding elements printed on the flexible substrate so that the at least two printed electrodes are located substantially between the two or more printed grounding elements.

10. The heart activity sensor structure of claim 4, wherein the flexible substrate comprises at least one through-hole, and corresponding at least one printed lead-through printed to the flexible substrate, wherein the at least one printed lead-through enables electrical coupling between the at least one printed grounding element and the printed electrostatic discharge shield.

11. The heart activity sensor structure of claim 1, further comprising a connection module for electrically coupling an electronics module with the at least two printed electrodes, wherein the connection module is electrically coupled with the at least two printed electrodes.

12. The heart activity sensor structure of claim 11, wherein the connection module is arranged on top of the printed electrostatic discharge shield.

13. The heart activity sensor structure of claim 11, wherein the flexible substrate and the printed electrostatic discharge shield comprise at least one through-hole, and corresponding at least one printed lead-through printed to at least one of the flexible substrate, and the printed electrostatic discharge shield, and wherein the at least one printed lead through enables electrical coupling between the at least two printed electrodes and the connection module.

14. The heart activity sensor structure of claim 11, wherein the electronics module is configured at least to transmit information related to the heart activity to a training computer.

15. The heart activity sensor structure of 11, wherein the electronics module is integrated as part of the heart activity sensor structure.

16. The heart activity sensor structure of claim 11, wherein the connection module comprises a base for detachably mounting the electronics module.

17. A method of manufacturing a heart activity sensor structure, comprising:
    printing a first layer comprising at least two printed electrodes on one side of a flexible substrate, the at least two printed electrodes being configured to be placed against a skin of a user in order to measure biometric signals related to heart activity;

providing a second layer comprising the flexible substrate, the flexible substrate being substantially non-conducting;

printing a third layer comprising a printed electrostatic discharge shield on an opposite side of the flexible substrate in relation to the at least two printed electrodes, the printed electrostatic discharge shield protecting the at least two printed electrodes from static electricity;

providing an insulation encompassing the third layer, the insulation comprising an electrically non-conducting material that provides electrical insulation between the second layer and the third layer;

providing at least two through holes in the second layer, the third layer, and the insulation; and providing one or more insulated conductors coupling to the electrodes through each of the at least two through holes.

18. The method of claim 17, further comprising printing at least one grounding element on a same side of the flexible substrate as the at least two printed electrodes, the at least one printed grounding element being electrically coupled, by printed electrical connection, to the printed electrostatic discharge shield and configured to contact the skin of the user.

19. The method of claim 17, further comprising providing at least one through-hole in the flexible substrate and the printed electrostatic discharge shield.

20. The method of claim 19, further comprising printing at least one printed lead-through, which corresponds to the at least one through-hole, to at least one of the flexible substrate and the printed electrostatic discharge shield, the at least one printed lead-through enabling electrical coupling between the at least two printed electrodes and a connection module.

* * * * *